United States Patent
Gutterer

(10) Patent No.: US 6,534,519 B1
(45) Date of Patent: *Mar. 18, 2003

(54) PHENANTHRIDINE-N-OXIDES WITH PDE-IV INHIBITING ACTIVITY

(75) Inventor: Beate Gutterer, Allensbach (DE)

(73) Assignee: Altana Pharma AG, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,146

(22) PCT Filed: Jan. 13, 2000

(86) PCT No.: PCT/EP00/00192

§ 371 (c)(1), (2), (4) Date: Jul. 12, 2001

(87) PCT Pub. No.: WO00/42034

PCT Pub. Date: Jul. 20, 2000

(30) Foreign Application Priority Data

Jan. 15, 1999 (EP) .............................................. 99100693

(51) Int. Cl.[7] ...................... A61K 31/473; A61P 11/08; C07D 221/12; C07D 471/04

(52) U.S. Cl. ...................... 514/298; 514/287; 514/289; 514/290; 514/291; 546/109; 546/108; 546/65; 546/74; 546/101

(58) Field of Search ................................. 546/109, 108, 546/65, 74; 514/298, 287, 289, 290

(56) References Cited

U.S. PATENT DOCUMENTS

| | | | | |
|---|---|---|---|---|
| 5,455,252 A | * | 10/1995 | Wilheim | 514/311 |
| 5,466,697 A | * | 11/1995 | Wilhelm | 514/300 |
| 5,475,003 A | * | 12/1995 | Wilheim | 514/290 |
| 5,545,647 A | * | 8/1996 | Tanaka | 514/343 |
| 6,008,215 A | | 12/1999 | Flockerzi | |
| 6,127,378 A | | 10/2000 | Gutterer | |
| 6,143,759 A | | 11/2000 | Flockerzi | |
| 6,191,138 B1 | | 2/2001 | Gutterer | |
| 6,306,863 B1 | | 11/2001 | Cooper et al. | 514/265.1 |
| 6,410,551 B1 | | 6/2002 | Gutterer | 514/290 |
| 6,436,952 B1 | | 8/2002 | Flockerzi | 514/292 |

FOREIGN PATENT DOCUMENTS

| | | |
|---|---|---|
| WO | WO 98/18796 | 5/1998 |
| WO | WO 98/55481 | 12/1998 |
| WO | WO 99/05111 | 2/1999 |

OTHER PUBLICATIONS

King FD. Medicinal Chemistry: Principles and Practice. The Royal Society of Chemistry. pp. 206–208 (1994).*

* cited by examiner

*Primary Examiner*—Evelyn Mei Huang
(74) *Attorney, Agent, or Firm*—Gary M. Nath; Todd L. Juneau; Joshua B. Goldberg

(57) ABSTRACT

The N-oxides of the compounds of formula (I), in which R1, R2, R3, R31, R4, R5, R51 and R6 have the meanings indicated in the description, are novel active bronchial therapeutics.

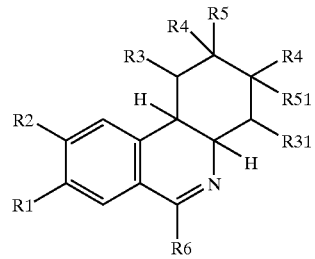

(I)

11 Claims, No Drawings

PHENANTHRIDINE-N-OXIDES WITH PDE-IV INHIBITING ACTIVITY

This application is a 371 of PCT/EP00/00192 filed Jan. 13, 2000.

FIELD OF APPLICATION OF THE INVENTION

The invention relates to novel N-oxides, which are used in the pharmaceutical industry for the production of medicaments.

KNOWN TECHNICAL BACKGROUND

Chem.Ber. 1939, 72, 675–677, J. Chem. Soc., 1956, 4280–4283 and J. Chem. Soc.(C), 1971, 1805 describe the synthesis of 6-phenylphenanthridines. The International Applications WO 97128131 and WO 97/35854 describe 6-phenyl- and 6-pyridylphenanthridines as PDE4 inhibitors.

DESCRIPTION OF THE INVENTION

It has now been found that the novel N-oxides of substituted 6-phenylphenanthridines described in greater detail below have surprising and particularly advantageous properties.

The invention thus relates to the N-oxides of the compounds of the formula I, $$\text{(I)}$$

in which

R1 is hydroxyl, 1-4C-alkoxy, 3-7C-cycloalkoxy, 3-7C-cycloalkylmethoxy or completely or predominantly fluorine-substituted 1-4C-alkoxy, R2 is hydroxyl, 1-4C-alkoxy, 3-7C-cycloalkoxy, 3-7C-cycloalkylmethoxy or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, or in which R3 and R31 together are a 1-4C-alkylene group, R4 is hydrogen or 1-4C-alkyl, R5 is hydrogen, R51 is hydrogen, or in which R5 and R51 together represent an additional bond, R6 is an R7-substituted phenyl radical, where R7 is a tetrazol-5-yl radical substituted by a radical R8, where R8 is hydrogen, 1-7C-alkyl, 3-7C-cycloalkyl, 3-7C-cycloalkylmethyl or Ar-1-4C-alkyl, where Ar is an unsubstituted or R9- and/or R10-substituted phenyl radical, and R9 and R10 independently of one another are halogen, nitro, cyano, 1-4C-alkyl, trifluoromethyl or 1-4C-alkoxy.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1-4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms are replaced by fluorine atoms.

1-2C-Alkylenedioxy represents, for example, the methylenedioxy [—O—CH$_2$—O—] and the ethylenedioxy [—O—CH$_2$—CH$_2$—O—] radicals.

If R3 and R31 together have the meaning 1-4C-alkylene, the positions 1 and 4 in the N-oxides of the compounds of the formula I are linked to one another by a 1-4C-alkylene bridge, 1-4C-alkylene representing straight-chain or branched alkylene radicals having 1 to 4 carbon atoms. Examples which may be mentioned are the radicals methylene [—CH$_2$—], ethylene [—CH$_2$—CH$_2$—], trimethylene [—CH$_2$—CH$_2$—CH$_2$], 1,2-dimethylethylene [—CH(CH$_3$)—CH(CH$_3$)—] and isopropylidene [—C(CH$_3$)$_2$—].

If R5 and R51 together are an additional bond, then the carbon atoms in positions 2 and 3 in the N-oxides of the compounds of the formula I are linked to one another via a double bond.

1-7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkylmethyl represents a methyl radical which is substituted by one of the abovementioned 3-7C-cycloalkyl radicals. Preferably, the 3-5C-cycloalkylmethyl radicals cyclopropylmethyl, cyclobutylmethyl and cyclopentylmethyl may be mentioned.

Ar-1-4C-alkyl represents one of the abovementioned 1-4C-alkyl radicals which is substituted by one of the aryl radicals defined above. Examples which may be mentioned are the p-methoxybenzyl, the phenethyl and the benzyl radicals.

Halogen within the meaning of the invention is bromine, chlorine or fluorine.

It is known to the person skilled in the art that the N-oxides according to the invention, when they are isolated, for example, in crystalline form, can contain various amounts of solvents. The invention therefore also includes all solvates and in particular all hydrates of the N-oxides according to the invention.

The N-oxides of the compounds of the formula I to be emphasized are those in which R1 is 1-2C-alkoxy, 3-5C-cycloalkoxy, 3-5C-cycloalkylmethoxy or completely or predominantly fluorine-substituted 1-2C-alkoxy, R2 is 1-2C-alkoxy, 3-SC-cycloalkoxy, 3-5C-cycloalkylmethoxy or completely or predominantly fluorine-substituted 1-2C-alkoxy, R3 is hydrogen, R31 is hydrogen, R4 is hydrogen or 1-2C-alkyl, R5 is hydrogen, R51 is hydrogen, or in which R5 and R51 together represent an additional bond, R6 is an R7-substituted phenyl radical, where R7 is a tetrazol-5-yl radical substituted by a radical R8, where R8 is 1-7C-alkyl, 3-7C-cycloalkyl, 3-7C-cycloalkylmethyl or Ar-1-4C-alkyl, where Ar is an unsubstituted or R9- and/or R10-substituted phenyl radical, and R9 and R10 independently of one another are 1-4C-alkyl or 1-4C-alkoxy.

The N-oxides of the compounds of the formula I particularly to be emphasized are those in which R1 is 1-2C-alkoxy, R2 is 1-2C-alkoxy, R3, R31, R4, R5 and R51 are hydrogen, R6 is an R7-substituted phenyl radical, where R7 is a tetrazol-5yl radical substituted by a radical R8, where R8 is 1-4C-alkyl, 5-7C-cycloalkyl, 3-7C-cycloalkylmethyl or Ar-1 -2C-alkyl, where Ar is an unsubstituted or R9-substituted phenyl radical, and R9 is 1-2C-alkyl or 1-2C-alkoxy.

Preferred N-oxides of the compounds of the formula I are those in which

R1 is 1-2C-alkoxy,

R2 is 1-2C-alkoxy,

R3, R31, R4, R5 and R51 are hydrogen,

R6 is an R7-substituted phenyl radical, where

R7 is an R8-substituted 2H-tetrazol-5-yl radical, and

R8 is 1-2C-alkyl.

The N-oxides of the compounds of the formula I are chiral compounds having chiral centers in positions 4a and 10b and, depending on the meaning of the substituents R3, R31, R4, R5 and R51, further chiral centers in the positions 1, 2, 3 and 4.

The invention therefore comprises all conceivable pure diastereomers and pure enantiomers and their mixtures in any mixing ratio, including the racemates. The N-oxides of the compounds of the formula I are preferred in which the hydrogen atoms in positions 4a and 10b are cis to one another. The pure cis enantiomers are particularly preferred.

In this connection, particularly preferred N-oxides of the compounds of the formula I are those in which positions 4a and 10b have the same absolute configuration as the compound (-)-cis-1,2-dimethoxy-4-(2-aminocyclohexyl)benzene employable as a starting compound and having the optical rotation $[\alpha]_D^{20}=-58.5°$ (c=1, ethanol).

The enantiomers can be separated in a manner known per se (for example by preparation and separation of appropriate diastereoisomeric compounds).

Preferably, an enantiomer separation is carried out at the stage of the starting compounds of the formula III

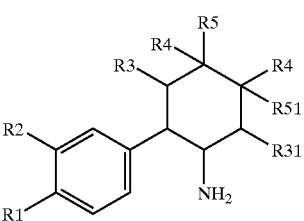

(III)

for example by means of salt formation of the racemic compounds of the formula III with optically active carboxylic acids. Examples which may be mentioned in this connection are the enantiomeric forms of mandelic acid, tartaric acid, O,O'-dibenzoyltartaric acid, camphoric acid, quinic acid, glutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formula III can also be prepared via asymmetric syntheses.

The tetrazol-5-yl radical R7 of the N-oxides of the compounds of the formula I can be bonded to the phenyl radical R6 either in the ortho, meta or para position to the phenanthridine ring.

Preferred N-oxides according to the invention are those in which the tetrazol-5-yl radical R7 is bonded to the phenyl radical R6 in the meta or para position to the phenanthridine ring. In this connection, the N-oxides according to the invention are particularly preferred in which the tetrazol-5-yl radical R7 is bonded in the para position.

The N-oxides of the compounds of the formula I can be prepared for example, by the process described below in greater detail.

The process comprises subjecting compounds of the formula I in which R1, R2, R3, R31, R4, R5, R51 and R6 have the meanings indicated above, to an N-oxidation.

The N-oxidation is carried out in a manner familiar to the person skilled in the art, e.g. with the aid of hydrogen peroxide in methanol or with the aid of N-chloroperoxybenzoic acid in dichloromethane at room temperature. The person skilled in the art will be familiar on the basis of his/her expert knowledge with the reaction conditions which are specifically necessary for carrying out the N-oxidation.

Compounds of the formula 1, in which R1, R2, R3, R31, R4, R5, R51, R6, R7 and R8 (R8≠H) have the meanings indicated above, can be prepared from the corresponding compounds of the formula II by a cyclocondensation reaction.

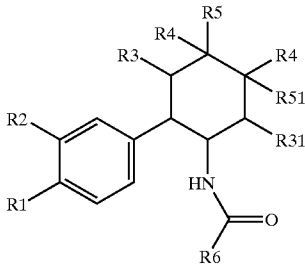

(II)

Compounds of the formula I in which R1, R2, R3, R31, R4, R5, R51, R6 and R7 have the meanings indicated above and R8 is hydrogen can be obtained from the corresponding compounds of the formula I in which R6 is cyanophenyl by reaction with alkali metal azides and halogen salts of ammonia. The 1H- and 2H-tetrazol-5-yl radicals of these compounds can then be subjected, optionally, to an alkylation reaction.

The alkylation reaction is expediently carried out analogously to the methods known to the person skilled in the art, e.g. by reaction of the 1H- or 2H-tetrazole compounds of the formula I with compounds of the formula R8-X in the presence of a base, where R8 has the abovementioned meanings—excluding hydrogen—and X is a suitable leaving group such as, for example, a chlorine, bromine or iodine atom or an alkylsulfate radical. The 1- and 2-substituted tetrazole regioisomer mixtures usually formed in the alkylation are separated by methods known to the person skilled in the art, such as crystallization or chromatography on suitable support materials. An analogous alkylation of tetrazoles and separation of the regioisomers is described, for example, in J. Med. Chem. 1996, 39, 2354.

The reaction of cyanophenyl derivatives with alkali metal azides and halogen salts of ammonia to give 2-, 3- or 4-(1H- or 2H-tetrazol-5-yl)phenyl derivatives which are unsubstituted in the tetrazole moiety is described, for example, in J. Med. Chem. 1993, 36, 3246.

The cyclocondensation is carried out in a manner known per se to the person skilled in the art, according to Bischler-Napieralski (e.g. as described in J. Chem. Soc., 1956, 4280–4282) in the presence of a suitable condensing agent, such as, for example, polyphosphoric acid, phosphorus pentachloride, phosphorus pentoxide or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Compounds of the formula II in which R1, R2, R3, R31, R4, R5, R51 and R6 have the meanings indicated above are accessible from the corresponding compounds of the formula III, in which R1, R2, R3, R31, R4, R5 and R51 have the meanings indicated above, by reaction with compounds of the formula R6-CO—X, in which R6 has the meaning indicated above and X represents a suitable leaving group, preferably a chlorine atom. For example, the benzoylation is carried out as described in the following examples according to the Einhorn process, the Schotten-Baumann variant or as in J. Chem. Soc. (C), 1971, 1805–1808.

Compounds of the formula R6-CO—X and compounds of the formula III are either known or can be prepared in a known manner.

Compounds of the formula R6-CO—X can be prepared, for example, from the corresponding carboxylic acids R6-COOH, in which R6 has the meaning indicated above, by reaction in a manner familiar to the person skilled in the art.

The compounds R6-COOH in which R6 has the meaning indicated above are either known or can be obtained from alkyl 2-, 3- or 4-cyanobenzoates in a manner known to the person skilled in the art, e.g. by reaction with alkali metal azides and halogen salts of ammonia to give alkyl 2-, 3- or 4-(1H- or 2H-tetrazol-5-yl)benzoates which are unsubstituted in the tetrazole moiety. Such a reaction is described, for example, in J. Med. Chem. 1993, 36, 3246. Optionally, these intermediate compounds can be converted—as described above for the 1H- or 2H-tetrazole compounds of the formula I or in the abovementioned literature—by alkylation with compounds of the formula R8-X in the presence of a base into alkyl R6-carboxylates in which R6 is an R7-substituted phenyl radical, R7 is an R8-substituted 1H- or 2H-tetrazol-5-yl radical and R8 is not hydrogen, but has one of the other meanings mentioned above for R8. The alkyl R6-carboxylates are converted into the free carboxylic acids R6-COOH by means of alkaline or acidic hydrolysis conditions familiar to the person skilled in the art.

The compounds of the formula III can be prepared, for example, from compounds of the formula IV,

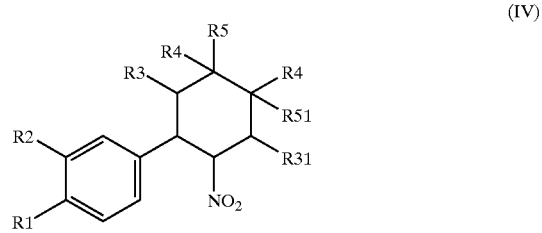

(IV)

in which R1, R2, R3, R31, R4, R5 and R51 have the abovementioned meanings, by reduction of the nitro group.

The reduction is carried out in a manner known to the person skilled in the art, for example as described in J. Org. Chem. 1962, 27, 4426 or as described in the following examples.

The reduction can be carried out, for example, by catalytic hydrogenation, e.g. in the presence of Raney nickel, in a lower alcohol such as methanol or ethanol at room temperature and under normal or elevated pressure. Optionally, a catalytic amount of an acid, such as, for example, hydrochloric acid, can be added to the solvent. Preferably, however, the reduction is carried out using metals such as zinc or iron with organic acids such as acetic acid or mineral acids such as hydrochloric acid.

The compounds of the formula III in which R1, R2, R3, R31 and R4 have the meanings indicated above and R5 and R51 together represent an additional bond can be prepared from the corresponding compounds of the formula IV by selective reduction of the nitro group in a manner known to the person skilled in the art, for example in the presence of Raney nickel in a lower alcohol as solvent using hydrazine hydrate as a hydrogen donor.

The compounds of the formula IV, in which R1, R2, R3, R31 and R4 have the meanings indicated above and R5 and R51 are hydrogen, are either known or can be prepared from corresponding compounds of the formula IV in which R5 and R51 together are an additional bond. The reaction can be carried out in a manner known to the person skilled in the art, preferably by hydrogenation in the presence of a catalyst, such as, for example, palladium on active carbon, e.g. as described in J. Chem. Soc. (C), 1971, 1805–1808.

The compounds of the formula IV, in which R5 and R51 together are an additional bond, are either known or can be obtained by the reaction of compounds of the formula (V),

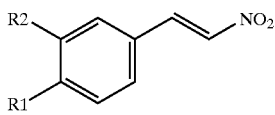

in which R1 and R2 have the meanings mentioned above, with compounds of the formula VI,

R3—CH=C(R4)—C(R4)=CH—R31 (VI)

in which R3, R31 and R4 have the meanings mentioned above.

Compounds of the formula IV, in which R5 and R51 together represent an additional bond and R3 and R31 together are a 1-4C-alkylene group can, for example, be obtained by reaction of cyclic compounds of the formula VI, in which R4 has the above-mentioned meanings and R3 and R31 together are a 1-4C-alkylene group [for example cyclohexa-1,3-dien, 2,3-dimethylcyclohexa-1,3-dien, cyclohepta-1,3-dien, 2,3-dimethylcyclohepta-1,3-dien or cycloocta-1,3-dien] with compounds of the formula V, in which R1 and R2 have the above-mentioned meanings.

The cycloaddition is in this case carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula IV obtained in the cycloaddition, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae V and VI are either known or can be prepared in a known manner. The compounds of the formula V can be prepared, for example, in a manner known to the person skilled in the art from corresponding compounds of the formula VII as described in, for example, J. Chem. Soc. 1951, 2524 or in J. Org. Chem. 1944, 9, 170 or as described in the following examples.

The compounds of the formula VII,

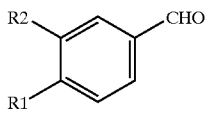

in which R1 and R2 have the meanings indicated above, are either known or can be prepared in a manner known to the person skilled in the art, as described, for example, in Ber. Dtsch. Chem. Ges. 1925, 58, 203.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1991.

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

The following examples serve to illustrate the invention further without restricting it. Likewise, further compounds of the formula 1, whose preparation is not explicitly described, can be prepared in an analogous manner or in a manner familiar per se to the person skilled in the art using customary process techniques.

In the examples, m.p stands for melting point, h for hour(s), RT for room temperature, EF for empirical formula, MW for molecular weight, calc. for calculated, fnd. for found. The compounds mentioned in the examples and their salts are a preferred subject of the invention.

EXAMPLES

Final Products 1. (−)-cis-6-[4-(2-Ethyl-2H-tetrazol-5-yl)phenyl]-8,9-dimethoxy-1,2,3,4,4a,10b-hexahydrophen-anthridine-N-5-oxide 1.0 g of (−)-cis-6-[4-(2-ethyl-2H-tetrazol-5-yl)phenyl]-8,9-dimethoxy-1,2,3,4,4a,10b-hexahydrophenanthridine (compound A1) are dissolved in 40 ml of methylene chloride and treated with 1–2 equivalents of m-chloroperoxybenzoic acid under a nitrogen atmosphere. The mixture is allowed to come to RT with stirring and, after the reaction is complete, the solvent is removed under reduced pressure. Purification is carried out by silica gel chromatography with ethylacetate/petroleum ether/triethylamine in the ratio 6/3/1. After solvent-evaporation of the product containing fractions 490 mg of the title compound of m.p. 143.5–146° C. are obtained.

EF: $C_{24}H_{27}N_5O_3$; MW: 433.52; Elemental analysis: calc.: C 66.50 H 6.28 N 16.15. Optical Rotation: fnd.: C 66.52 H 6.37 N 16.24.

$[\alpha]_D^{20} = -30°$ (c = 0.5, ethanol)

Starting Compounds

A1. (−)cis-6-[4-(2-Ethyl-2H-tetrazol-5-yl)phenyl]-8,9-dimethoxy-1,2,3,4,4a,10b-hexahydrophen-anthridine 6.5 g of (−)-cis-N-[2-(3,4-dimethoxyphenyl)cyclohexyl]-4-(2-ethyl-2H-tetrazol-5-yl)benzamide (compound B1) are dissolved in 200 ml of acetonitrile and 3.0 ml of phosphoryl chloride and the solution is stirred at 80° C. for 4 h. The reaction mixture is concentrated under reduced pressure and the residue is treated with sodium hydrogencarbonate solution and extracted with ethyl acetate. The organic phase is dried using sodium sulfate and concentrated. After chromatography on silica gel using petroleum ether (low)/ethyl acetate/triethylamine in the ratio 6/3/1, 3.28 g of the title compound are obtained as a solidifying oil.

EF: $C_{24}H_{27}N_5O_2$; MW: 417.52; Elemental analysis×0.12 $H_2O$: calc.: C 68.62 H 6.55 N 16.67. Optical Rotation: fnd. C 68.63 H 6.81 N 16.59.

$[\alpha]_D^{20} = -75.2°$ (c = 0.2, ethanol)

B1. (−)-cis-N-[2-(3,4-Dimethoxyphenyl)cyclohexyl]-4-(2-ethyl-2H-tetrazol-5-yl)benzamide 3.0 g of (−)-cis-1,2-dimethoxy-4-(2-aminocyclohexyl) benzene (compound C2) are dissolved in 100 ml of methylene chloride and 3.0 ml of triethylamine. A solution of 3.0 g of 4-(2-ethyl-2-H-tetrazol-5-yl)benzoyl chloride in 50 ml of methylene chloride is added dropwise at RT and the mixture is extracted, after stirring for 2 h, with 100 ml each of water, 2N hydrochloric acid, satd. sodium hydrogencarbonate solution and water again. The organic phase is dried using sodium sulphate and concentrated. The residue is taken up in petroleum ether (low)/ethyl acetate in the ratio 2/1, filtered off with suction and dried. 5.2 g of the title compound of m.p. 188–192° C. are obtained.

Optical Rotation:

$$[\alpha]_D^{20} = -195.5° \ (c = 0.2, \text{ethanol})$$

C1 (+/−)-cis-1,2-Dimethoxy4-(2-aminocyclohexyl)benzene 125 g of (+/−)-cis-1,2-dimethoxy-4-(2-nitrocyclohexyl)benzene and 120 g of zinc powder or granules are suspended in 1300 ml of ethanol. 220 ml of acetic acid are added dropwise at boiling heat. The precipitate is filtered off with suction and washed with ethanol, and the filtrate is concentrated under reduced pressure. The residue is taken up in hydrochloric acid and extracted with toluene. The aqueous phase is rendered alkaline using 50% strength sodium hydroxide solution, the precipitate is filtered off with suction and the filtrate is extracted with toluene. The organic phase is dried using sodium sulfate and concentrated. 98 g of the title compound are obtained as a crystallizing oil.

Alternatively 8.5 g of (+/−)-cis-1,2-dimethoxy-4-(2-nitrocyclohexyl)benzene are dissolved in 400 ml of methanol and treated at RT with 7 ml of hydrazine hydrate and 2.5 g of Raney nickel in portions in the course of 8 h. After stirring overnight at RT, the reaction mixture is filtered, the filtrate is concentrated and the residue is chromatographed on silica gel using a mixture of toluene/ethyl acetate/triethylamine=4/2/0.5. The title compound is obtained as an oil.

C2. (−)-cis-1,2-Dimethoxy4-(2-aminocyclohexyl)benzene 12.0 g of (+/−)-cis-1,2-dimethoxy-4-(2-aminocyclohexyl)benzene and 6.2 g of (−)-mandelic acid are dissolved in 420 ml of dioxane and 60 ml of tetrahydrofuran and the solution is stirred overnight at RT. The solid is filtered off with suction, dried, treated with 100 ml of saturated sodium hydrogencarbonate solution and extracted with ethyl acetate. The organic phase is dried using sodium sulphate and concentrated under reds ed pressure. 4.8 g of the title compound are obtained of m.p.: 80–81.50° C.

Optical rotation:

$$[\alpha]_D^{20} = -58.5° \ C. \ (c = 1, \text{ethanol}).$$

D1. (+/−)-cis1,2-Dimethoxy-4-(2-nitrocyclohexyl)benzene 8.4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of 10% strength Pd/C. The reaction mixture is filtered and the filtrate is concentrated. M.p.: 84–86.5° C.

D2. (+/−)-cis-1,2-Dimethoxy-4-(2-nitrocyclohex-4-enyl)benzene 10.0 9 of (+/−)-trans-1,2-dimethoxy-4-(2-nitrocyclohex-4-enyl)benzene and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 11 of ice water, the precipitate is filtered off with suction, washed with water and dried, and the crude product is recrystallized from ethanol. 8.6 g of the title compound of m.p. 82.5–84° C. are obtained.

D3. (+/−)-trans-1,2-Dimethoxy-4-(2-nitrocyclohex4-enyl)benzene 50.0 9 of 3,4-dimethoxy-ω-nitrostyrene and 1.0 g (9.1 mmol) of hydroquinone are suspended in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5–115.5° C.

E1. 3,4-Dimethoxy-ω-nitrostyrene 207.0 g of 3,4-dimethoxybenzaldehyde, 100.0 g of ammonium acetate and 125 ml of nitromethane are heated to boiling for 3–4 h in 1.01 of glacial acetic acid. After cooling in an ice bath, the precipitate is filtered off with suction, rinsed with glacial acetic acid and petroleum ether and dried. M.p.: 140–141° C. Yield: 179.0 g.

Commercial Applicability

The N-oxides according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The N-oxides according to the invention are distinguished here by low toxicity, good enteral absorption (high bioavailability), a large therapeutic breadth and the absence of significant side-effects.

On account of their PDE-inhibiting properties, the N-oxides according to the invention can be employed in human and veterinary medicine as therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias. endogenous and exogenous acne, acne rosacea and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gramnegative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the N-oxides according to the invention can be employed for the treatment of diabetes insipidus and disorders in connection with disturbances of brain metabolism, such as, for example, cerebral senility, senile dementia (Alzheimer's dementia), multiinfarct dementia or alternatively disorders of the CNS, such as, for example, depressions or arteriosclerotic dementia.

A further subject of the invention is a process for the treatment of mammals, including man, which are suffering from one of the abovementioned illnesses. The process comprises administering to the sick mammal a therapeutically efficacious and pharmacologically tolerable amount of one or more of the N-oxides according to the invention.

The invention further relates to the N-oxides according to the invention for use in the treatment and/or prophylaxis of illnesses, in particular the illnesses mentioned.

The invention likewise relates to the use of the N-oxides according to the invention for the production of medicaments which are employed for the treatment and/or prophylaxis of the illnesses mentioned.

Medicaments for the treatment and/or prophylaxis of the illnesses mentioned, which contain one or more of the N-oxides according to the invention, are furthermore a subject of the invention.

A further subject of the invention is a commercial product, consisting of a customary secondary pack, a primary pack containing the medicament (for example an ampoule or a blister pack) and, optionally, a pack insert, the medicament exhibiting antagonistic action against cyclic nucleotide phosphodiesterases of type 4 (PDE4) and leading to the attenuation of the symptoms of illnesses which are connected with cyclic nucleotide phosphodiesterases of type 4, and the suitability of the medicament for the prophylaxis or treatment of illnesses which are connected with cyclic nucleotide phosphodiesterases of type 4 being indicated on the secondary pack and/or on the pack insert of the commercial product, and the medicament containing one or more N-oxides of the compounds of the formula I according to the invention. The secondary pack, the primary pack containing the medicament and the pack insert otherwise comply with what would be regarded as standard to the person skilled in the art for medicaments of this type.

The medicaments are prepared by processes which are known per se and familiar to the person skilled in the art. As medicaments, the N-oxides according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the N-oxides according to the invention are preferably also administered by inhalation. For this, these are either administered directly as a powder (preferably in micronized form) or by nebulization of solutions or suspensions which contain them. With respect to the preparations and administration forms, reference is made, for example, to the details in European Patent 163 965.

For the treatment of dermatoses, the N-oxides according to the invention are in particular used in the form of those medicaments which are suitable for topical application. For the production of the medicaments, the N-oxides according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of PDE4 inhibition at the cellular level, the activation of inflammatory cells has particular importance. As an example, the FMLP (N-formyl-methionyl-leucyl-phenylalanine)-induced superoxide production of neutrophilic granulocytes may be mentioned, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc. New York-Basle-Hong Kong)].

Substances which inhibit chemoluminescence and cytokine secretion and the secretion of inflammatory mediators on inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to an increase in the intracellular cyclic AMP concentration and thus to the inhibition of cell activation. PDE4 inhibition by the substances according to the invention is thus a central indicator of the suppression of inflammatory processes (Glembycz M A, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE 3/4 inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and Ca; NaunynSchmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160. "The Handbook of Immunopharmacology", Academic Press, 1996).

Inhibition of PDE4 Activity

Methodology

The activity test can be carried out, for example according to the method of Bauer and Schwabe. For this, the method is adapted to microtiter plates (Naunyn-Schmiedeberg's Arch. Pharmacol. 1980, 311, 193–198). The PDE reaction takes place in the first step here. In a second step, the resulting 5'-nucleotide is cleaved by a 5'-nucloetidase of the snake venom of Crotalus atrox to the uncharged nucleoside. In the third step, the nucleoside is separated from the remaining charged substrate on ion-exchange columns. The columns are eluted directly into minivials, into which 2 ml of scintillator fluid are additionally added for counting, using 2 ml of 30 mM ammonium formate (pH 6.0).

The inhibitory values determined for the compounds according to the invention [inhibitory concentration as –log $IC_{50}$ (mol/1)] follow from the following Table A, in which the numbers of the compounds correspond to the numbers of the examples.

TABLE A

Inhibition of the PDE4 activity

| Compound | –log $IC_{50}$ |
|---|---|
| 1 | 6.29 |

What is claimed is:
1. An N-oxide of the compound of formula I,

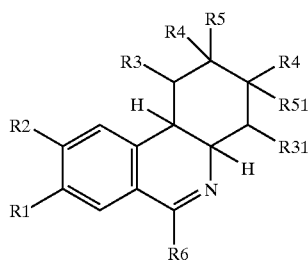

(I)

in which

R1 is hydroxyl, 1-4C-alkoxy, 3-7C-cycloalkoxy, 3-7C-cycloalkylmethoxy or completely or predominantly fluorine-substituted 1-4C-alkoxy, R2 is hydroxyl, 1-4C-alkoxy, 3-7C-cycloalkoxy, 3-7C-cycloalkylmethoxy or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, or in which R3 and R31 together are a 1-4C-alkylene group, R4 is hydrogen or 1-4C-alkyl, R5 is hydrogen, R51 is hydrogen, or in which R5 and R51 together represent an additional bond, R6 is an R7-substituted phenyl radical, where R7 is a tetrazol-5-yl radical substituted by a radical R8, where R8 is 1-7C-alkyl, 3-7C-cycloalkyl, 3-7C-cycloalkylmethyl or Ar-1-4C-alkyl, where Ar is an unsubstituted or R9- and/or R10-substituted phenyl radical, and R9 and R10 independently of one another are halogen, nitro, cyano, 1-4C-alkyl, trifluoromethyl or 1-4C alkoxy.

2. An N-oxide of the compound of formula I as claimed in claim 1, in which

R1 is 1-2C-alkoxy, 3-5C-cycloalkoxy, 3-5C-cycloalkylmethoxy or completely or predominantly fluorine-substituted 1-2C-alkoxy, R2 is 1-2C-alkoxy, 3-5C-cycloalkoxy, 3-5C-cycloalkylmethoxy or completely or predominantly fluorine-substituted 1-2C-alkoxy, R3 is hydrogen, R31 is hydrogen, R4 is hydrogen or 1-2C-alkyl, R5 is hydrogen, R51 is hydrogen, or in which R5 and R51 together represent an additional bond;

R6 is an R7-substituted phenyl radical, where

R7 is a tetrazol-5-yl radical substituted by a radical R8, where

R8 is 1-7C-alkyl, 3-7C-cycloalkyl, 3-7C-cycloalkylmethyl or Ar-1-4C-alkyl, where Ar is an unsubstituted or R9- and/or R10-substituted phenyl radical, and R9 and R10 independently of one another are 1-4C-alkyl or 1-4C-alkoxy.

3. An N-oxide of the compound of formula I as claimed in claim 1, in which

R1 is 1-2C-alkoxy,

R2 is 1-2C-alkoxy,

R3, R31, R4, R5 and R51 are hydrogen,

R6 is an R7-substituted phenyl radical, where

R7 is a tetrazol-5-yl radical substituted by a radical R8, where

R8 is 1-4C-alkyl, 5-7C-cycloalkyl, 3-7C-cycloalkylmethyl or Ar-1-2C-alkyl, where Ar is an unsubstituted or R9-substituted phenyl radical, and R9 is 1-2C-alkyl or 1-2C-alkoxy.

4. An N-oxide of the compound of formula I as claimed in claim 1, in which
R1 is 1-2C-alkoxy,
R2 is 1-2C-alkoxy,
R3, R31, R4, R5 and R51 are hydrogen,
R6 is an R7-substituted phenyl radical, where
R7 is an R8-substituted 2H-tetrazol-5-yl radical, and
R8 is 1-2C-alkyl.

5. An N-oxide of the compound of formula I as claimed in claim 1, which has the same absolute configuration in positions 4a and 10b as the compound (−)-cis-1,2-dimethoxy-4-(2-aminocyclohexyl)benzene having the optical rotation $$[\alpha]_D^{20} = -58.5°$$

(c=1, ethanol) which is used as the starting material.

6. A method for treating an illness treatable with a PDE IV inhibitor in a patient comprising administering to said patient a therapeutically effective PDE-IV inhibiting amount of the N-oxide of the compound of formula I as claimed in claim 1.

7. A pharmaceutical composition comprising at least one N-oxide of the compound of formula I as claimed in claim 1 together with pharmaceutically acceptable excipients and/or vehicles.

8. A method for treating airway disorders in a patient comprising administering to said patient a therapeutically effective amount of the N-oxide of the compound of formula I as claimed in claim 1.

9. The method according to claim 6, wherein said illness treatable with a PDE IV inhibitor is selected from the group consisting of acute airway disorders, chronic airway disorders, dermatoses, arthritic disorders, and disorders of the upper airway.

10. The method according to claim 9, wherein said illness treatable with a PDE IV inhibitor is selected from the group consisting of asthma prophylaxis, bronchitis, allergic bronchitis, bronchial asthma, emphysema, COPD, psoriasis vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea, rheumatoid arthritis, rheumatoid spondylitis, osteoarthritis, septic shock, endotoxin shock, gram-negative sepsis, toxic shock syndrome, adult respiratory distress syndrome (ARDS), Crohn's disease, ulcerative colitis, allergic rhinitis, allergic sinusitis, chronic rhinitis, chronic sinusitis, allergic conjunctivitis, nasal polyps, cardiac insufficiency, erectile dysfunction, colics of the kidneys, and colics of the ureter.

11. The method according to claim 6, wherein said illness treatable with a PDE IV inhibitor is selected from the group consisting of asthma prophylaxis, bronchitis, allergic bronchitis, bronchial asthma, emphysema, COPD, allergic rhinitis, allergic sinusitis, chronic rhinitis, chronic sinusitis, allergic conjunctivitis and nasal polyps.

* * * * *

UNITED STATES PATENT AND TRADEMARK OFFICE
CERTIFICATE OF CORRECTION

PATENT NO. : 6,534,519 B1
DATED : March 18, 2003
INVENTOR(S) : Gutterer

It is certified that error appears in the above-identified patent and that said Letters Patent is hereby corrected as shown below:

Column 16,
Line 6, after "The method according to" and before "wherein said illness", please replace "9" with -- 6 --.
Line 10, before "vulgaris)", please insert -- ( --.

Signed and Sealed this

Fifteenth Day of July, 2003

JAMES E. ROGAN
*Director of the United States Patent and Trademark Office*